United States Patent [19]
Keil et al.

[11] Patent Number: 5,888,356
[45] Date of Patent: Mar. 30, 1999

[54] INHIBITION OF POLYMERIZATION OF VINYLAROMATIC OR VINYLALIPHATIC

[75] Inventors: Thomas Keil, Bottrop; Manfred Kaufhold, Marl; Bernd Helpap, Recklinghausen, all of Germany

[73] Assignee: Huels Aktiengesellschaft, Marl, Germany

[21] Appl. No.: 946,006

[22] Filed: Oct. 7, 1997

Related U.S. Application Data

[63] Continuation-in-part of Ser. No. 511,472, Aug. 4, 1995, abandoned.

[30] Foreign Application Priority Data

Aug. 19, 1994 [DE] Germany ............... 44 29 485.9
Apr. 27, 1995 [DE] Germany ............ 195 15 450.9

[51] Int. Cl.$^6$ ............... B01D 3/10; B01D 3/34; C07C 7/20
[52] U.S. Cl. ............ 203/8; 203/9; 203/91; 585/5; 585/860; 585/864; 585/952; 560/205; 560/218
[58] Field of Search ............ 203/8, 9, 99, 100, 203/91; 560/205, 218; 585/3–5, 864, 860, 952; 252/397, 401, 399, 403–405, 407

[56] References Cited

U.S. PATENT DOCUMENTS

| | | | |
|---|---|---|---|
| 3,494,967 | 2/1970 | Bailey | 570/104 |
| 3,527,822 | 9/1970 | Benson, Jr. | 203/9 |
| 4,654,451 | 3/1987 | Miller et al. | 585/5 |
| 4,670,131 | 6/1987 | Thomas M. Ferrell . | |
| 5,155,148 | 10/1992 | Parker et al. | 524/83 |
| 5,254,760 | 10/1993 | Roland A. E. Winter, et al. . | |
| 5,322,960 | 6/1994 | Kazuhiko Sakamoto, et al. . | |
| 5,468,789 | 11/1995 | Lewis et al. | 524/99 |

FOREIGN PATENT DOCUMENTS

| | | |
|---|---|---|
| 2619906 | 11/1976 | Germany . |
| 0320217 | 12/1993 | Japan . |

*Primary Examiner*—Virginia Manoharan
*Attorney, Agent, or Firm*—Oblon, Spivak, McClelland, Maier & Neustadt, P.C.

[57] ABSTRACT

The polymerization of a vinylaromatic or vinylaliphatic compound at elevated temperature in the absence of air is inhibited by processing the vinylaromatic or vinylaliphatic compound in the presence of 4-hydroxy-2,2,6,6-tetramethylpiperidine-N-oxyl or 4-acetylamino-2,2,6,6-tetramethylpiperidine-N-oxylalone or in admixture with p-nitrosophenol or 2-methyl-4-nitrosophenol.

9 Claims, No Drawings

INHIBITION OF POLYMERIZATION OF VINYLAROMATIC OR VINYLALIPHATIC

This application is a Continuation of application Ser. No. 08/511,472, filed on Aug. 4, 1995, now abandoned.

BACKGROUND OF THE INVENTION

1. Field of the Invention

The invention relates to a process of inhibiting the polymerization of vinylaromatic or vinylaliphatic compounds, especially styrene, during distillation.

2. Discussion of the Background

Styrene is the starting product for the preparation of polystyrene and mixed polymers. Due to the incomplete reaction and formation of by-products in the preparation of styrene, distillative separation is necessary. Since the styrene easily polymerizes thermally at the distillation temperatures, an inhibitor must be added to the process. Such inhibitors, e.g., nitrophenols, nitrosophenols, p-tert-butylpyrocatechol, or sulfur, are known and are also used on a large scale. From the publications U.S. Pat. No. 4,967,027 and European Patent No. B-0,229,515, it can be further concluded that combinations of different inhibitors can also be used.

Due to its thermal sensitivity, on a large scale, styrene is distilled in vacuum without exception. It is known that most inhibitors need the presence of oxygen to be effective.

In principle, this produces the problem of making available sufficient oxygen in a column operated in vacuum.

There is therefore a need for new polymerization inhibitors for vinylaromatic or vinylaliphatic compounds that are suitable for use at increased temperatures as they are used under distillation conditions and that do not have the indicated disadvantages.

SUMMARY OF THE INVENTION

Accordingly, one object of this invention is to provide a method of effectively inhibiting the polymerization of vinylaromatic and vinylaliphatic compounds during distillation.

Briefly, this object and other objects of the invention as hereinafter will become more readily apparent, can be attained in a method of inhibiting the polymerization of vinylaromatic and vinylaliphatic compounds at elevated temperatures under an atmosphere which excludes air by processing the vinylaromatic or vinylaliphatic compound in the presence of an inhibitor which is 4-hydroxy-2,2,6,6-tetramethylpiperidine-N-oxyl or 4-acetylamino-2,2,6,6,-tetramethylpiperidine-N-oxyl alone or in admixture with p-nitrosophenol or 2-methyl-4-nitrosophenol.

DETAILED DESCRIPTION OF THE PREFERRED EMBODIMENTS

It has been surprisingly found that the inhibitors 4-hydroxy-2,2,6,6-tetramethylpiperidine-N-oxyl (HTMPO) and 4-acetylamino-2,2,6,6-tetramethylpiperidine-N-oxyl (AA-TEMPO), alone or in combination with p-nitrosophenol or 2-methyl-4-nitrosophenol, have good inhibitory properties, even with the exclusion of oxygen, in inhibiting the polymerization of vinylaromatic or vinylaliphatic compounds at increased temperatures.

In German Patent No. 2,804,449, general reference is made to the effectiveness of nitroso compounds in the distillation of vinylaromatic monomer compounds. The 2,6-dinitro-p-cresol that is protected in this case has the disadvantage, as do nitrocresols generally, that these compounds are retardants. Retardants slow down polymer formation but cannot prevent it completely so that small polymer amounts are always formed. In contrast to the retardants, inhibitors prevent polymer formation completely over a certain period of time depending on their effectiveness, but have no effect thereafter.

HTMPO and AA-TEMPO are known as radical traps in radical-induced styrene polymerization. However, the finding of an extraordinarily good inhibitory effect in styrene distillation in vacuum was surprising. Additionally, it has been found, surprisingly, that the combinations of 2-methyl-4-nitrosophenol/HTMPO, p-nitrosophenol/HTMPO, 2-methyl-4-nitrosophenol/AA-TEMPO, and p-nitrosophenol/AA-TEMPO exhibit synergistic effects in the inhibition both with oxygen, as well as without oxygen, i.e., the effect of the mixtures is better than the effect of HTMPO or AA-TEMPO alone. An especially strong synergism exists in the combination of p-nitrosophenol/HTMPO and p-nitrosophenol/AA-TEMPO. Here, a 50% mixture has an extraordinarily good effect.

For the process of the invention, styrene, substituted styrene (e.g., α-methylstyrene), acrylic acid esters, methacrylic acid esters, and divinylbenzene can be used.

The greatest effectiveness is attained by the inhibitors or inhibitor mixtures of the invention at a temperature of 90° to 140° C., preferably 100° to 120° C. The amount of inhibitor added can be varied as a function of the distillation conditions. Usually, the degree of stabilization is proportional to the amount of inhibitor added.

It was determined that HTMPO and AA-TEMPO, alone or in combination with p-nitrosophenol or 2-methyl-4-nitrosophenol in amounts of 50 to 200 ppm, preferably in amounts of 100 to 150 ppm, based on the vinylaromatic or vinylaliphatic compound, produce the best results.

This primarily depends on the temperature of the distillation mixture and the desired degree of inhibition.

If HTMPO or AA-TEMPO is used with p-nitrosophenol or 2-methyl-4-nitrosophenol, the mixing ratio is 90:10 to 10:90, preferably 50:50.

The preparation of the inhibitors of the invention is known from the literature (e.g., DE-OS [Offenlegungsschrift=Disclosure)] 4,219,459 and Annalen 417, p. 120).

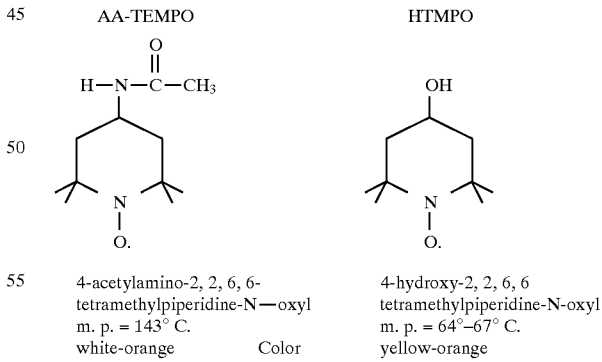

| AA-TEMPO | HTMPO |
|---|---|
| 4-acetylamino-2, 2, 6, 6-tetramethylpiperidine-N—oxyl | 4-hydroxy-2, 2, 6, 6 tetramethylpiperidine-N-oxyl |
| m. p. = 143° C. | m. p. = 64°–67° C. |
| white-orange    Color | yellow-orange |

Having generally described this invention, a further understanding can be obtained by reference to certain specific examples which are provided herein for purposes of illustration only and are not intended to be limiting unless otherwise specified.

The effectiveness of the inhibitors or inhibitor mixtures was determined by gravimetric polymer determination according to the following procedure:

A 300 ml amount of freshly distilled styrene together with the inhibitor to be studied were heated to 110° C. with stirring in a 500-ml three-necked flask and the time was recorded. Samples were periodically taken and the polymer content was gravimetrically determined by precipitation with methanol. In this manner, "polymer vs. time" curves were obtained wherein the time until a polymer content of 3% was obtained was chosen as a measure of the effectiveness of the inhibitor or inhibitor mixture. The experiments were done under nitrogen atmosphere (nitrogen was constantly bubbled in). The results are shown in Table I.

TABLE I

Retention times of styrene at 100° C. until a polymer content of 3% under nitrogen was achieved with the use of different inhibitors.

| Inhibitor | | Residence time to 3% polymer formation |
|---|---|---|
| Styrene not inhibited | | 48 min |
| HTMPO | 50 ppm | 107 min |
| HTMPO | 100 ppm | 128 min |
| p-Nitrosophenol | 50 ppm | 122 min |
| p-Nitrosophenol | 100 ppm | 176 min |
| 2-Methyl-4-nitrosophenol | 50 ppm | 169 min |
| HTMPO/ p-Nitrosophenol | 50 ppm 50 ppm | 184 min |
| HTMPO/ 2-Methyl-4-nitrosophenol | 50 ppm 50 ppm | 197 min |
| AA-TEMPO | 50 ppm | 102 min |
| AA-TEMPO | 100 ppm | 123 min |
| AA-TEMPO/ 2-Methyl-4-nitrosophenol | 50 ppm 50 ppm | 184 min |
| AA-TEMPO/ 2-Methyl-4-nitrosophenol | 75 ppm 25 ppm | 162 min |
| AA-TEMPO/ p-Nitrosophenol | 50 ppm 50 ppm | 169 min |

In addition, HTMPO and AA-TEMPO, compared with the nitrosophenols, have the advantage of better storage stability and lower toxicity. Additionally, these materials do not tend to decompose spontaneously.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method of inhibiting the polymerization of a vinylaromatia or vinylaliphatic compound, comprising:
vacuum distilling said vinylaromatic or vinylaliphatic compound at an elevated temperature of 90°–140° C. under conditions which exclude air in the presence of an inhibitor which is a) 4-acetylamino-2,2,6,6-tetramthylpiparidine-N-oxyl, b) 4-acetylamino-2,2,6,6-tetramethylpiparidine-N-oxyl mixed with p nitrosophenol or c) 4-acetylamino-2,2,6,6-tetramethylpiperidine-N-oxyl mixed with 2-methyl-4-nitrosopheno.

2. The process according to claim 1, wherein 4-acetylamino-2,2,6,6-tetramethylpiperidine-N-oxyl is mixed with p-nitrosophenol or 2-methyl-4-nitrosophenol in a ratio ranging from 90:10 to 10:90.

3. The process according to claim 2, wherein said ratio is 50:50.

4. The process according to claim 1, wherein a) 4-acetylamino-2,2,6,6-tatramethylpiperidine-N-oxyl, b) 4-acetylamino-2,2,6,6-tetramethylpiperidine-N-oxyl mixed with p-nitrosophenol or c) 4-acetylamino-2,2,6,6-tetramethylpiperidine-N-oxyl mixed with 2-methyl-4-nitrosophenol is present in an amount of from 50 to 200 ppm, based on the inylaromatic or vinylaliphatic compound.

5. The process according to claim 1, wherein said elevated temprature ranges from 90° to 12° C.

6. The process according to claim 1, wherein said vinylaromatic compound is styrene, a substituted styrene or divinylbonzen, and said vinylaliphatic compound is an acrylic acid enter or a methacrylic acid ester.

7. A method of inhibiting the polymerization of a vinylaromatic or vinylaliphatic compound, comprising:
vacuum distilling said vinylaromatic or vinylaliphatic compound at an elevated temperature of 90°–14020 C. under conditions which exclude air in the presence of an inhibitor which is 4-hydroxy-2,2,6,6-tetramethylpiperidine-N-oxyl in admixture with p-nitrosophenol or 2-methyl-4-nitrosophonol, wherein the ratio of the piperidine-N-oxyl compound to said nitrosophenol compound ranges from 90:10–10:90.

8. The process according to claim 7, wherein said 4-hydroxy-2,2,6,6-tatramethylpiperidine-N-oxyl in admixture with p-nitrosopheno or 2-methyl-4-nitrosophenol is present in an amount of from 50 to 200 ppm, based on the vinylaromatic or vinylaliphatic compound.

9. The process of claim 7, wherein said vinylaromatic compound is divinylbenzene, styrene or a substituted styrene and said vinylaliphatic compound is an acrylic acid aster or a methacrylic acid ester.

* * * * *

UNITED STATES PATENT AND TRADEMARK OFFICE
CERTIFICATE OF CORRECTION

PATENT NO. : 5,888,356
DATED : March 30, 1999
INVENTOR(S) : Thomas KEIL, et al.

It is certified that error appears in the above-indentified patent and that said Letters Patent is hereby corrected as shown below:

On the title page, item [54], and on top of column 1, the last word of the title is missing. It should be:

--COMPOUNDS--

Signed and Sealed this

Twenty-eighth Day of September, 1999

*Attest:*

Q. TODD DICKINSON

*Attesting Officer*   Acting Commissioner of Patents and Trademarks